(12) United States Patent
Kunitsky et al.

(10) Patent No.: US 7,728,082 B2
(45) Date of Patent: *Jun. 1, 2010

(54) METHODS FOR PREPARING POLYMERS FROM PHENOLIC MATERIALS AND COMPOSITIONS RELATING THERETO

(75) Inventors: Keith Joseph Kunitsky, West Grove, PA (US); Michael Thomas Sheehan, Corpus Christi, TX (US); James Ralph Sounik, Corpus Christi, TX (US); Mark Elliot Wagman, Wilmington, DE (US)

(73) Assignee: DuPont Electronic Polymers L.P., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/381,742

(22) Filed: Mar. 16, 2009

(65) Prior Publication Data

US 2009/0176947 A1 Jul. 9, 2009

Related U.S. Application Data

(63) Continuation of application No. 11/880,305, filed on Jul. 21, 2007, now Pat. No. 7,521,526.

(60) Provisional application No. 60/834,652, filed on Aug. 1, 2006.

(51) Int. Cl.
*C08F 2/06* (2006.01)
*C07C 37/50* (2006.01)
*C08F 112/14* (2006.01)

(52) U.S. Cl. .......... 526/75; 526/204; 526/220; 526/222; 526/313; 568/649; 568/650; 568/662

(58) Field of Classification Search ........ 568/750, 568/649, 650, 662; 526/75, 313, 204, 220, 526/222

See application file for complete search history.

(56) References Cited

U.S. PATENT DOCUMENTS

| 4,101,590 | A | 7/1978 | Sato et al. |
|---|---|---|---|
| 4,517,349 | A | 5/1985 | Fujiwara et al. |
| 5,959,051 | A | 9/1999 | Kaneko et al. |
| 6,258,901 | B1 | 7/2001 | Kaneko et al. |
| 7,521,526 | B2 * | 4/2009 | Kunitsky et al. ............ 528/498 |
| 2005/0228191 | A1 | 10/2005 | Kunitsky et al. |

OTHER PUBLICATIONS

D. Munteanu, C. Csunderlik and I. Tincul, Synthesis of the Monomeric Antioxidant 3,5-di-tert-butyl-4-hydroxy-styrene by the thermal decomposition of trans-3,5-di-tert-butyl-4-hydroxycinnamic acid, Journal of Thermal Analysis 37 (1991), pp. 411-426.

* cited by examiner

*Primary Examiner*—Fred M Teskin
(74) *Attorney, Agent, or Firm*—James J. Mullen

(57) ABSTRACT

A process for producing a stable polymer such as poly(hydroxystyrene) which comprises the decarboxylation of a corresponding phenolic in the presence of a non-amine basic catalyst and a polar organic solvent, followed by the polymerization thereof.

1 Claim, No Drawings

US 7,728,082 B2

METHODS FOR PREPARING POLYMERS FROM PHENOLIC MATERIALS AND COMPOSITIONS RELATING THERETO

RELATED PATENT APPLICATIONS

This patent application is a continuation of patent application U.S. Ser. No. 11/880,305 filed Jul. 21, 2007, now U.S. Pat. No. 7,521,526 B2, and which clams benefit of provisional patent application 60/834,852 filed Aug. 1, 2006.

BACKGROUND OF THE INVENTION

1. Field of the Invention

The present invention relates broadly to processes useful in the synthesis of poly(hydroxystyrenes) and other hydroxyl-containing polymers and copolymers. More specifically, the processes of the present invention are directed to the modification and polymerization of a phenolic precursor material.

2. Background of the Invention

Munteanu et al, Journal of Thermal Analysis, v37, n2, p 411 (1991) is directed to the thermal decomposition of trans-3,5-di-tert-butyl-4-hydroxycinnamic acid to synthesize a monomeric antioxidant 3,5-di-tert-butyl-4-hydroxystyrene. Decarboxylation in solid state or in aqueous solution was accompanied by polymerization of the styrenic products.

Kunitsky et al, US Published Patent Application No. 2005-0228191, commonly assigned, is directed to base catalyzed thermal decarboxylation of phenolic materials to provide vinylphenols capable of being acetylated.

Methods for the preparation of poly(hydroxystyrene)s are known. However, a need exists for converting phenolic materials into stable poly(hydroxystyrenes) in relatively high yield and high purity.

SUMMARY OF THE INVENTION

This invention relates to a process for the production of stable polymers and co-polymers of poly(hydroxystyrene) comprising the steps of: providing a phenolic substrate providing a reaction mixture comprising: a non-amine basic catalyst; and at least one polar organic solvent; contacting the phenolic substrate with the reaction mixture at a temperature of at least about 100° C. for a time sufficient for the decarboxylation of the phenolic substrate to form a stable decarboxylated hydroxystyrene intermediate; and contacting the decarboxylated hydroxystyrene intermediate and polar organic solvent with a polymerization initiator at a temperature and time sufficient to produce a poly(hydroxystyrene) or a copolymer thereof.

DETAILED DESCRIPTION OF THE PREFERRED EMBODIMENT(S)

The invention provides a multi-step method for preparing poly(hydroxystyrenes) via a thermal, non-amine base-catalyzed decarboxylation of phenolic substrates followed by polymerization of the decarboxylated hydroxystyrene intermediate. Poly(hydroxystyrene)s have utility as resins, elastomers, adhesives, coatings, automotive finishes, inks and electronic materials.

The following definitions are used herein and should be referred to for interpretation of the claims and the specification.

"p" means para as in para-hydroxystyrene.

"pAS" is the abbreviation used for para-acetoxystyrene which is also represented as p-acetoxystyrene or 4-acetoxystyrene.

"pHCA" is the abbreviation used for para-hydroxycinnamic acid which is also represented as p-hydroxy cinnamic acid or 4-hydroxy cinnamic acid.

"pHS" is the abbreviation used for para-hydroxystyrene which is also represented as p-hydroxystyrene or 4-hydroxystyrene. Alternatively, the abbreviation "HSM" is used for 4-hydroxystyrene.

"CA" means cinnamic acid.

The term "yield" as used herein refers to the amount of product produced in a chemical reaction. The yield is typically expressed as a percentage of the theoretical yield for the reaction. The term "theoretical yield" means the predicted amount of product to be expected based on the amount of substrate initially present and the stoichiometry of the reaction.

The term "polar" as applied to solvents of the invention refers to solvents characterized by molecules having permanent dipole moments.

The term "aprotic" as applied to the solvents of the invention refers to a solvent that is incapable of acting as a labile proton donor or acceptor.

The term "protic" as applied to the solvents of the invention refers to a solvent that is capable of acting as a labile proton donor or acceptor.

The term "polar organic solvent mixture" refers to a mixture of organic solvents comprising at least one polar solvent.

The term "aprotic, polar organic solvent mixture" refers to a mixture of organic solvents comprising at least one aprotic, polar solvent.

"TAL" is the abbreviation used for tyrosine ammonia lyase.

"PAL" is the abbreviation used for phenylalanine ammonia lyase.

"PAH" is the abbreviation used for phenylalanine hydroxylase.

The term "TAL activity" refers to the ability of a protein to catalyze the direct conversion of tyrosine to pHCA.

The term "PAL activity" refers to the ability of a protein to catalyze the conversion of phenylalanine to cinnamic acid.

"pal" represents a gene that encodes an enzyme with PAL activity.

"tal" represents a gene that encodes an enzyme with TAL activity.

The term "PAL/TAL activity" or "PAL/TAL enzyme" refers to a protein, which contains both PAL and TAL activity. Such protein has at least some specificity for both tyrosine and phenylalanine as an enzymatic substrate.

The term "P-450/P-450 reductase system" refers to a protein system responsible for the catalytic conversion of cinnamic acid to pHCA. The P-450/P450 reductase system is one of several enzymes or enzyme systems known in the art that performs a cinnamate 4-hydroxylase function. As used herein the term "cinnamate 4-hydroxylase" will refer to the general enzymatic activity that results in the conversion of cinnamic acid to pHCA, whereas the term "P450/P450 reductase system" will refer to a specific binary protein system that has cinnamate 4-hydroxylase activity.

VAZO® 52 is the trade name for 2,2'-azo bis(2,4-dimethylpentanenitrile).

VAZO® 67 is the trade name for 2,2'-azo bis(2-methylbutanenitrile).

VAZO® 88 is the trade name for 1,1'-azo bis(cyclohexanecarbonitrile).

LUPEROX® 26 is the trade name for t-butyl peroxy-2-ethylhexanoate.

All ranges given herein include the end of the ranges and also all the intermediate range points.

Phenolics

Phenolics useful in the present invention can have the structure:

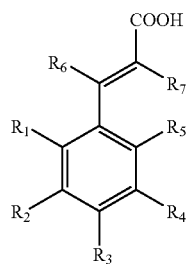

wherein $R_1$, $R_3$, and $R_5$ are H, OH, or $OCH_3^-$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH, and $R_2$ and $R_4$ are not both simultaneously t-butyl. Examples of suitable phenolics include, but are not limited to, 4-hydroxycinnamic acid, ferulic acid, sinapinic acid, caffeic acid, 2-hydroxycinnamic acid, 3,5-dimethyl-4-hydroxycinnamic acid, and α-cyano-4-hydroxycinnamic acid. High yields of the decarboxylated product were obtained even with non-sterically hindered phenol materials or substrates, which are oftentimes more prone to product decomposition than sterically hindered phenols. Sterically hindered phenols are herein defined as phenols having large, bulky groups, such as t-butyl, at both $R_2$ and $R_4$ positions. Non-sterically hindered phenols are phenols that do not have large, bulky groups at both $R_2$, and $R_4$ positions. Non-sterically hindered phenol substrates include, but are not limited to, phenols wherein at least one of $R_2$ or $R_4$ is H, OH, $OCH_3$, methyl, ethyl, or propyl. High yields of decarboxylated product are generally obtained even with ortho unsubstituted phenol substrates, which can also be prone to product decomposition. Ortho unsubstituted phenols are herein defined as phenols wherein at least one of $R_2$ or $R_4$ is H.

These phenolic precursor materials or substrates of the present invention may be obtained in a number of ways. For example, 4-hydroxycinnamic acid (pHCA), predominantly in the trans form, is available commercially from companies such as Aldrich (Milwaukee, Wis.) and TCI America (Portland, Oreg.). Additionally, pHCA may be prepared by chemical synthesis using any method known in the art. For example, pHCA may be obtained by reacting malonic acid with para-hydroxybenzaldehyde as described by Pittet et al. in U.S. Pat. No. 4,316,995, or by Alexandratos in U.S. Pat. No. 5,990,336. Alternatively, pHCA may also be isolated from plants (R. Benrief et al. *Phytochemistry* 47:825-832 (1998) and U.S. Patent Application Publication No. 20020187207). In one embodiment, the source of pHCA is from bioproduction using a production host. In another embodiment, the production host is a recombinant host cell, which may be prepared using standard DNA techniques. These recombinant DNA techniques are described by Sambrook, J., Fritsch, E. F. and Maniatis, T. *Molecular Cloning: A Laboratory Manual*, Second Edition, Cold Spring Harbor Laboratory Press, Cold Spring Harbor, N.Y. (1989), incorporated herein by reference.

In one embodiment, pHCA is produced as described by Qi et al. in U.S. Patent Application Publication No. 20030079255, incorporated herein by reference. According to that disclosure, pHCA may be produced using a recombinant microorganism engineered to express at least one gene encoding a phenylalanine hydroxylase (PAH) activity and at least one gene encoding a tyrosine ammonia lyase (TAL) activity. This transformed microorganism metabolizes a fermentable carbon source, such as glucose, to phenylalanine, which is converted to tyrosine by PAH. The tyrosine produced is converted to pHCA by the TAL enzyme. Any suitable enzyme possessing a TAL activity may be used. For example, an enzyme having both PAL and TAL (PAL/TAL) activity may be used. TAL enzymes, produced through mutagenesis of wild-type yeast PAL enzymes to have enhanced TAL activity, may also be used, as described by Gatenby et al. in U.S. Pat. No. 6,368,837. Alternatively, an inducible TAL enzyme from the yeast *Trichosporon cutaneum*, as described by Breinig et al. in U.S. Patent Application Publication No. 20040023357 or a bacterial TAL enzyme such as that described by Kyndt et al. (*FEBS Lett.* 512:240-244 (2002)) or by Huang et al. in U.S. Patent Application Publication No. 20040059103 may be used.

In another embodiment, pHCA is produced by any one of the methods disclosed by Gatenby et al. supra, incorporated herein by reference. For example, pHCA may be produced using a recombinant microorganism engineered to express a gene encoding a yeast PAL activity and genes encoding a plant P450/P-450 reductase system. This transformed microorganism metabolizes a fermentable carbon source, such as glucose, to phenylalanine, which is converted to cinnamic acid (CA) by the PAL enzyme. CA is subsequently converted to pHCA by the action of the P-450/P450 reductase system. Alternatively, pHCA may be produced using a recombinant microorganism expressing a gene encoding a TAL activity. The TAL enzyme converts tyrosine directly to pHCA. Any suitable TAL enzyme may be used, as described supra.

In another embodiment, pHCA is produced using a two-stage fermentation as described by Ben-Bassat in U.S. Patent Publication No. 2005-0260724, incorporated herein by reference. The first stage comprises providing a microbial production host having an enhanced ability to produce the aromatic amino acid tyrosine (an over-producer). These cells are grown at physiological pH to a point where tyrosine is accumulated in the growth medium. During the second stage of the fermentation the cells are contacted with a source of TAL at a pH of about 8.0 to about 11.0. During this stage tyrosine is converted to pHCA at relatively high rates and yields. Alternatively, the two stages may be done as two separate steps, wherein the tyrosine is isolated from the fermentation medium of the first step and then is contacted with the source of TAL.

For the bioproduction of pHCA, the microorganism to be used is cultured in a fermentor in a suitable growth medium. Any suitable fermentor may be used including a stirred tank fermentor, an airlift fermentor, a bubble fermentor, or any combination thereof. Materials and methods for the maintenance and growth of microbial cultures are well known to those in the art of microbiology or fermentation science (See for example, Bailey et al., *Biochemical Engineering Fundamentals*, second edition, McGraw Hill, New York, 1986). The bioproduced pHCA may be isolated from the fermentation medium for use in the invention using methods known in the art. For example, solids may be removed from the fermentation medium by centrifugation. Then, the pHCA may be precipitated by acidification of the medium and recovered by centrifugation. If desired, the pHCA may be further purified, for example, using organic solvent extraction.

Similarly, ferulic acid, sinapinic acid, and caffeic acid are available commercially from companies such as Aldrich (Milwaukee, Wis.) and TCI America (Portland, Oreg.). Alternatively, as these substrates are all natural plant products, comprising elements of the lignin biosynthetic pathway, they may be readily isolated from plant tissue (see for example Jang et al., *Archives of Pharmacal Research* (2003), 26(8), 585-590; Matsufuji et al., *Journal of Agricultural and Food Chemistry* (2003), 51(10), 3157-3161; WO 2003046163; Couteau et al, *Bioresource Technology* (1998), 64(1), 17-25; and Bartolome et al., *Journal of the Science of Food and Agriculture* (1999), 79(3), 435-439). Additionally, methods of chemical synthesis are known for a number of the more common phenolic substrates (see for example WO 2002083625 ("Preparation of ferulic acid dimers and their pharmaceutically acceptable salts, and use thereof for treating dementia") JP 2002155017 ("Preparation of caffeic acid from ferulic acids"); and Taniguchi et al., *Anticancer Research* (1999), 19(5A), 3757-3761). The preparation of alkylated pHCA derivatives is described by Lala et al. in Australian Patent Application No. 7247129.

Non-Amine Basic Catalysts

The method of the invention makes use of a non-amine basic catalyst or similar type material. A non-amine basic catalyst is any basic compound capable of facilitating the present reactions that does not contain amines. (By way of comparison examples of amine containing catalysts are pyridine and ethylenediamine.) Virtually any non-amine basic catalyst may be used that is compatible with the reaction conditions of the invention, where metallic salts and particularly potassium salts or acetate salts are preferred. Catalysts particularly suitable in the present invention include, but are not limited to, potassium acetate, potassium carbonate, potassium hydroxide, sodium acetate, sodium carbonate, sodium hydroxide and magnesium oxide.

All of the non-amine catalysts of the invention are available commercially from, for example, EM Science (Gibbstown, N.J.) or Aldrich (Milwaukee, Wis.).

The optimum concentration of non-amine basic catalyst will vary depending on the concentration of substrate, nature of the solvent used and reaction conditions. Thus any amount can be used which facilitates the reaction. Preferred concentrations are from about 0.001 mol % to about 30 mol %, relative to the substrate, in the reaction mixture; most preferred are from about 1% to about 30%.

Organic Solvents

For the decarboxylation reaction alone, a wide variety of organic solvents may be used, including both aprotic, polar organic solvents and protic, polar organic solvents. A single protic, polar solvent or a single aprotic, polar solvent may be used. Additionally, mixtures of aprotic, polar solvents; mixtures of protic, polar solvents; mixtures of aprotic and protic polar solvents; and mixtures of aprotic or protic solvents with nonpolar solvents may be used; wherein aprotic, polar solvents or mixtures thereof are preferred. Suitable aprotic, polar solvents include, but are not limited to, N,N-dimethylformamide, 1-methyl-2-pyrrolidinone, N,N-dimethylacetamide, dimethylsulfoxide, hexamethylphosphoramide, and hexamethylphosphorous triamide. Suitable protic, polar solvents include, but are not limited to, di(propylene glycol) methyl ether (Dowanol™ DPM), di(ethylene glycol) methyl ether, 2-butoxyethanol, ethylene glycol, 2-methoxyethanol, propylene glycol methyl ether, n-hexanol, and n-butanol.

For the two-step decarboxylation-polymerization process, organic solvents preferably have the net characteristics of being both aprotic and polar. A single aprotic, polar solvent may be used, or a mixture of aprotic, polar solvents may be used. Alternatively, an aprotic, polar solvent may be used in combination with a non-polar solvent. Solvents particularly suitable in the two step process of the invention include, but are not limited to, N,N-dimethylformamide, 1-methyl-2-pyrrolidinone, N,N-dimethylacetamide, dimethylsulfoxide, hexamethylphosphoramide, and hexamethylphosphorous triamide.

Surprisingly, the hydroxystyrene intermediate obtained by the decarboxylation reaction is generally very stable when dissolved in the solvents of the invention. Generally, little or no oligomerization of the hydroxystyrene occurs; polymerization inhibitors including, but not limited to, hydroquinone, hydroquinone monomethylether, and 4-tert-butyl catechol, and polymerization retarders including, but not limited to, aromatic nitro compounds such as dinitro-ortho-cresol and dinitrobutylphenol may be admixed with the phenolic substrate prior to commencing the decarboxylation reaction. In some cases, no polymerization inhibitor or retarder is used. This surprising stability of the hydroxystyrene intermediate when dissolved in the solvents of the invention, even at high concentrations, provides the benefits of higher yield, higher purity of the hydroxystyrene intermediate and results in a very stable polymer, having a higher molecular weight, and lower cost to produce.

Kunitsky et al teach the acetylation of the hydroxystyrene, for example, reacting acetic anhydride with p-hydroxystyrene to produce p-acetoxystyrene. The skilled practitioner understands that pAS is significantly more stable that pHS, and that commercial poly(hydroxystyrenes) are produced by polymerizing pAS with subsequent removal of the protecting group. The surprising stability of the present invention hydroxystyrene intermediate when dissolved in the solvents used in this invention, lowers costs by rendering the acetylation step and subsequent deprotection step unnecessary.

The stability obtained is especially surprising in light of related art such as U.S. Pat. No. 4,517,349 "it is very difficult to obtain p-vinyl phenol having high purity by purification of the resulting crude p-vinyl phenols."; U.S. Pat. No. 5,453,483 states that "The process . . . does not directly utilize 4-hydroxystyrene which is difficult to isolate since it readily decomposes and is toxic by skin absorption."; and U.S. Pat. No. 5,959,051 relates that "vinylphenol monomer is very difficult to store, because it is rapidly polymerized even at room temperature." The present invention thus solves a long felt need in the art.

Decarboxylation Reaction Conditions

Generally, the phenolic materials, the non-amine basic catalyst, and the organic solvent are added to a reaction vessel to form a reaction mixture. Any suitable reaction vessel may be used.

Reaction temperatures may vary depending on the concentration of substrate, the stability of the product formed, choice of catalyst and yield desired. Typically, temperatures of at least about 100° C. are suitable where temperatures in the range of at least about 100° C. to about 200° C. are consistent with effective production of product. (If yields and reaction rates are not an issue, then temperatures between 30° C. and 100° C. can be used where appropriate). For the reaction using 4-hydroxycinnamic acid as substrate, the preferred temperature range is from about 120° C. to about 150° C. For substrates that give a less stable product, e.g., caffeic acid, lower temperatures in the range of about 100° C. to about 120° C. are used. Higher temperatures in the range of about 150° C. to about 200° C. may be used with substrates that give a more stable product, e.g., 3,5-dimethyl-4-hydroxycinnamic acid.

The reaction may be carried out at a pressure ranging from less than atmospheric pressure to about 1000 psig (6895 kPa); in addition, a pressure of about 500 psig (3447 kPa) may be used. The pressure may be adjusted using an inert gas such as nitrogen. For reactions at elevated pressures, any conventional pressure reaction vessel may be used including, but not limited to, shaker vessels, rocker vessels, and stirred autoclaves. Operating at reduced pressures may facilitate removal of carbon dioxide from the reaction mixture.

There is no limit on the time for the reaction; however, most reactions will run in less than six hours and reaction times of about 45 minutes to about 240 minutes are typical.

The intermediate product at this point is a very stable hydroxystyrene solution, typically comprising a) a hydroxystyrene having the general structure:

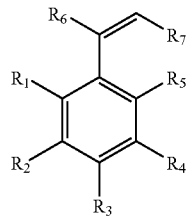

wherein $R_1$, $R_3$, and $R_5$ are H, OH, or $OCH_3^-$; $R_2$, and $R_4$ are H, OH, $OCH_3$ or linear or branched alkyl; $R_6$ and $R_7$ are H, halo, or cyano provided that at least one of $R_1$, $R_3$, or $R_5$ is OH, and that $R_2$, and $R_4$ are not both simultaneously t-butyl; and b) an organic solvent, such as a polar organic solvent.

Optional Concentration or Dilution of Decarboxylated Product

The reaction mixture obtained from the decarboxylation reaction may be further processed without adjusting the concentration of the decarboxylated hydroxystyrene intermediate in the solvent. As is well known in the polymerization art, varying the concentration of the monomer prior to performing the polymerization reaction affects the molecular weight of the polymer obtained.

In one embodiment the reaction mixture obtained from the decarboxylation reaction is further processed in the polymerization reaction without changing the concentration.

In another embodiment the reaction mixture obtained from the decarboxylation reaction is concentrated, as by a distillation operation, before it is further processed in the polymerization reaction.

In another embodiment the reaction mixture obtained from the decarboxylation reaction is diluted, by adding one or more additional solvents as previously defined, before it is further processed in the polymerization reaction.

Optional Co-Monomers

The reaction mixture obtained from the decarboxylation reaction may be further processed in the polymerization reaction to provide a homopolymer. Alternatively, one or more monomers may be added to produce a copolymer. Additional monomers are known in the art and include, without limitation, (1) styrene and substituted styrenes such as divinylbenzene, 4-methylstyrene, pentafluorostyrene, styrene alkoxide wherein the alkyl portion is $C_1$-$C_5$ straight or branched chain and the like; (2) acrylates such as methyl acrylate, ethyl acrylate, lauryl acrylate, 2-hydroxyethyl acrylate, t-butyl acrylate, MM-methyl adamantyl acrylate, ETCDA-ethyl tricyclodecanyl acrylate, cyclohexylacrylate and the like; (3) methacrylates and dimethacrylates such as methyl methacrylate, lauryl methacrylate, stearyl methacrylate, 2-ethylhexyl methacrylate, MAMA—methyl adamantyl methacrylate, EAA—ethyl adamantyl acrylate, EAMA—ethyl adamantyl methacrylate, ETCDMA—ethyl tricyclodecanyl methacrylate, PAMA—propyl adamantyl methacrylate, MBAMA—methoxybutyl adamantyl methacrylate, MBAA—methoxylbutyl adamantyl acrylate, isobornylacrylate, isobornylmethacrylate, cyclohexylmethacrylate and the like; (4) polymerizable fluorine-containing compounds such as fluoroalkylsubstituted acrylates and methacrylates including compounds sold by DuPont under the ZONYL® name with general structure $CH_2\!=\!CHCO_2CH_2CH_2(CF_2)_nCF_3$ and $CH_2\!=\!C(CH_3)CO_2CH_2CH_2(CF_2)_nCF_3$, and the like; and (5) other co-monomers such as acrylic acid, methacrylic acid, maleic acid, fumaric acid, maleic anhydride, acrylonitrile, acrylamides, methacrylamides, and the like. Other monomers that can be used within the scope of the present invention include, for example, those monomers set forth in U.S. Pat. No. 6,800,419 and U.S. Pat. No. 6,838,225, both of which are incorporated herein by reference.

Polymerization Initiators

The free radical initiator may be any initiator that achieves the desired end result. The initiator may be selected from the group consisting of 2,2'-azobis(2,4-dimethylpentanenitrile), 2,2'-azobis(2-methylpropanenitrile), 2,2'-azobis(2-methylbutanenitrile), 1,1'-azobis(cyclohexanecarbonitrile), t-butyl peroxy-2-ethylhexanoate, t-butyl peroxypivalate, t-amyl peroxypivalate, diisononanoyl peroxide, decanoyl peroxide, succinic acid peroxide, di(n-propyl) peroxydicarbonate, di(sec-butyl) peroxydicarbonate, di(2-ethylhexyl) peroxydicarbonate, t-butylperoxyneodecanoate, 2,5-dimethyl-2,5-di(2-ethylhexanoylperoxy)hexane, t-amylperoxyneodecanoate, dimethyl 2,2'-azobisisobutyrate and combinations thereof.

As a preferred embodiment, the initiator is selected from the group consisting of 2,2'-azobis(2,4-dimethylpentanenitrile), 2,2'-azobis(2-methylbutanenitrile), 1,1'-azobis(cyclohexanecarbonitrile), and combinations thereof.

The amount of initiator is any amount that accomplishes the desired end result and is selected based upon factors including concentration of monomer, identity and amount of co-monomer(s), temperature, solvent and desired molecular weight.

As taught in US Patent Publication Nos. 2004-171777 and US2004-024132 chain transfer agents such as thiocarbonylthio compounds may be used in the polymerization reaction in a process called Reversible Addition Fragmentation (chain) Transfer (RAFT) polymerization.

Polymerization Reaction Conditions

The polymerization conditions are any temperature and pressure that will produce the desired end result. In general, the temperatures are from about 30° C. to about 100° C., preferably from about 40° C. to about 100° C., and most preferably from about 45° C. to about 90° C. The pressure may be atmospheric, sub-atmospheric or super-atmospheric. The polymerization time is not critical, but generally will take place over a period of at least one minute to about 15 hours in order to produce a polymer of desired molecular weight.

All reagents, including the initiator, optional co-monomer(s) and optional additional solvent(s) may be added to the decarboxylated hydroxystyrene intermediate and solvent mixture in the reactor prior to commencing the polymerization reaction, or alternatively may be fed to the reactor as the reaction proceeds, such as metered feed of one or more co-monomers to achieve higher compositional uniformity, or alternatively or additionally adding additional initiator to achieve higher conversion of all monomer(s).

Conducting the polymerization reaction in a reactor fitted with a reflux condenser provides the benefit of additional heat transfer area to remove the polymerization exotherm. The solvent and the operating pressure may be selected so that the boiling point of the polymerization reaction mixture is the desired temperature. The pressure may be changed as desired over the course of the polymerization. An additional solvent, or mixture thereof, may be added to affect boiling point or other aspects of the polymerization.

Optional Isolation or Purification of Poly(Hydroxystyrene)

After the polymerization reaction the polymer may be subjected to a purification procedure such as that described in U.S. Pat. No. 6,864,324 wherein the same type organic solvent (first solvent) is used to purify the polymer via a multi-step fractionation process. Additionally, a second solvent such as toluene (and as described in U.S. Pat. No. 6,864,324) can be added to the polymer mixture and processed in a similar manner.

This optional purification utilizes a second solvent which is immiscible with the solvent utilized for the polymerization reaction. The second solvent is added to the poly(hydroxystyrene) mixture until a second layer is formed. The mixture is then stirred vigorously or is heated to boiling for several minutes and then allowed to stand until cool. A discrete second layer is formed which is then removed by decantation or similar means, and the process is repeated until no further purification is identified, as for example, until a small sample of the decanted solvent upon evaporation to dryness shows no residue. In this fashion, there are removed by-products and low weight average molecular weight materials.

The polymer solution is then subjected to distillation to remove the remaining second solvent. Most often removal of the second solvent is accomplished by azeotropic distillation; the azeotropic mixture boiling below the boiling temperature of either the first or the second solvent.

Typical second solvents useful for the method of this step include toluene, hexane, heptane, octane, petroleum ether, ligroin, lower alkyl halohydrocarbons, i.e., methylene chloride, and the like.

One of the important measures of the degree of impurity of the crude polymer produced from the polymerization of the monomers is the polydispersity value. In general, it is desirable to have a low value, for example, less than about 3; the lower value is indicative that the polymerization reaction was more uniform in chain length. The uniqueness of this purification step is that the desired polymer formed is, to some degree, not soluble in the solvent and that the undesired, low molecular weight average polymers and undesired monomers are soluble in the solvent. Thus the purification/fractionalization provides the removal of these undesirable materials. In general, the polydispersity of the crude polymer is measured before, during and after this purification/fractionalization step, with the objective of reducing this value by at least about 10% of what the value of the original crude polymer was before the purification treatment. Preferably, it is desirable to yield a product whose polydispersity is below about 2.0. It is to be understood that polydispersity means the ratio of weight average molecular weight (Mw) over the number average molecular weight (Mn) as determined by Gel Permeation Chromatography (GPC).

The poly(hydroxystyrene) may be isolated by techniques such as filtration and drying if a solid product is desired. If a solution is the desired form then the solvent may be exchanged for a third organic solvent, which may be a photoresist compatible solvent, and the first solvent is removed by distillation. This third solvent is at least one member selected from glycol ethers, glycol ether acetates and aliphatic esters having no hydroxyl or keto group. Examples of the solvent include glycol ether acetates such as ethylene glycol monoethyl ether acetate and propylene glycol monomethyl ether acetate (PGMEA) and esters such as ethyl-3-ethoxypropionate, methyl-3-methoxypropionate, among which PGMEA is preferred. These solvents may be used alone or in the form of a mixture thereof.

Further examples of the third solvent include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, .gamma.-butyrolactone, propylene glycol methyl ether acetate, propylene glycol ethyl ether acetate, propylene glycol propyl ether acetate, methyl lactate, ethyl lactate, propyl lactate, and tetramethylene sulfone. Of these, the propylene glycol alkyl ether acetates and alkyl lactates are especially preferred. The solvents may be used alone or in admixture of two or more. An exemplary useful solvent mixture is a mixture of a propylene glycol alkyl ether acetate and an alkyl lactate. It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred.

Usually the solvent is used in amounts of about 300 to 2,000 parts, preferably about 400 to 1,000 parts by weight per 100 parts by weight of the solids in the chemically amplified positive resist composition. The concentration is not limited to this range as long as film formation by existing methods is possible.

As previously described, the poly(hydroxystyrenes) and co-polymers thereof generally have a wide range of application and uses. These include, without limitation, photoresist compositions (U.S. Pat. No. 5,852,128), curing agents, varnishes, printing inks, tackifiers for rubber, crude oil separator, solder mask, photoimageable coverlay for rigid or flexible printed circuit boards, epoxy materials, epoxy or blocked isocyanate containing paint formulations, highly viscous polymers, micro electromechanical systems, toner resins for use in photocopying, antireflective coatings, chemically and thermally resistant protective coatings, and the like.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and, without departing from the spirit and scope thereof, can make various changes and modifications of the invention to adapt it to various uses and conditions.

The meaning of abbreviations used is as follows: "min" means minute(s), "h" means hour(s), "mL" means milliliter(s), "L" means liter(s), "nm" means nanometer(s), "mol" means mole(s), "mmol" means millimole(s), "9" means gram(s), "mg" means milligram(s) "M" means molar concentration, "mol %" means mole percent, "wt %" means percent by weight, "Pa" means pascal(s), "kPa" means kilopascal(s), "psig" means pounds per square inch gauge, "MHz" means megahertz, "HPLC" means high performance liquid chromatography, "GPC" gel permeation chromatography, "NMR" means nuclear magnetic resonance spectrometry, "FTIR" means Fourier transform infrared spectrophotometry, "GC" means gas chromatography, "DMF" means N,N-dimethylformamide, "DMAc" means N,N-dimethylacetamide, "Mw" means weight-average molecular weight, and "Mn" means number-average molecular weight.

General Methods:

Reagents:

4-Hydroxycinnamic acid was obtained from TCI America (Portland, Oreg.), unless otherwise noted. All solvents were reagent grade and were obtained from EMD Chemicals, Inc. (Gibbstown, N.J.) as was the ACS reagent grade, anhydrous sodium carbonate. Potassium acetate was ACS reagent grade, anhydrous and was obtained from Aldrich (Milwaukee, Wis.). Vazo® 52, 67 and 88 initiators were obtained from E.I. du Pont de Nemours and Co. (Wilmington, Del.). Luperox® 26 initiator was obtained from Elf Atofina. (Philadelphia, Pa.).

Analytical Methods:

HPLC Methods:

Method 1: An Agilent 1100 HPLC system (Agilent Technologies, Wilmington, Del.) was used with a reverse-phase Zorbax® XDB-C18 column, 2.1×50 mm (supplied by Agilent Technologies). The HPLC separation was achieved using a gradient combining two solvents: Solvent A, HPLC grade water+0.05% trifluoroacetic acid, and Solvent B, HPLC grade acetonitrile+0.05% trifluoroacetic acid. The gradient was 95% A to 0% A over 4.5 minutes, hold 0.5 minute, then return to initial conditions. The mobile phase flow rate was 0.8 mL/min. A temperature of 60° C. and a sample injection of 1 µL were used.

Method 2: The Agilent 1100 HPLC system was used with a reverse-phase Zorbax SB-C18 column (4.6 mm×150 mm, 3.5 µm, supplied by Agilent Technologies). The HPLC separation was achieved using a gradient combining two solvents: Solvent A, 0.1% trifluoroacetic acid in HPLC grade water and Solvent B, 0.1% trifluoroacetic acid in acetonitrile. The gradient was 95% A to 100% A over 10 minutes, hold 2 minutes, then return to initial conditions over 2.5 minutes. The mobile phase flow rate was 1.0 mL/min. A temperature of 40° C. and a sample injection of 1 µL were used.

Suitable calibration curves were generated using standard pHCA and HSM solutions. The HSM for the standards was prepared from acetoxystyrene using a method similar to that described by Leuteritz et al. (*Polymer Preprints* 43(2):283-284 (2002)). The calibration curves were used to determine wt % of pHCA and HSM in each sample from HPLC peak areas. With this information and the total weight of the reaction mixture at each time (including a correction for the loss of $CO_2$ upon decarboxylation), the weight and moles of pHCA and HSM versus time were calculated.

$^1$H NMR:

The proton NMR data were obtained using a Bruker DRX (Bruker NMR, Billerica, Mass.) at 500 MHz.

GC Method:

An HP Gas Chromatograph 5890 Series II (Hewlett-Packard Co., Palo Alto, Calif.) was used with a J&W Scientific, DB-1 (30 m×0.25 mm×0.25 µm) column, a cup-type packed injection liner, and a flame ionization detector. The column flow rate of helium gas was 1.2 mL/min. Inlet temperature was 2000 and detector temperature was 2850. Injection volume was 1 µl. The GC separation was achieved with the following temperature program with a 20 min. total run time: initial temperature of 600 for 1 minute; increasing 20°/minute to a final temperature of 2800, and holding at that temperature for 8 minutes.

An injection of solvent was made prior to sample injection. Both a standard and samples were diluted in DMF prior to injection to provide suitable peak intensity. The syringe was washed with solvent multiple times before and after injection.

GPC:

GPC was performed on a Waters gel permeation chromatograph equipped with a refractive index detector.

Example 1

Decarboxylation of 4-Hydroxycinnamic Acid Followed by In Situ Polymerization of 4-Hydroxystyrene in N,N-dimethylformamide The purpose of this Example was to demonstrate the synthesis of poly(4-hydroxystyrene) (PHS) in a one-pot, two-step process from 4-hydroxycinnamic acid (pHCA).

4-Hydroxycinnamic acid (5 g), 7 mL of N,N-dimethylformamide (DMF, reagent grade), and 0.3 g of potassium acetate were charged into a 25-mL round-bottom flask equipped with a reflux condenser, magnetic stirring, and nitrogen. The reaction solution was heated at 135° C. in an oil bath for 90 min. After this time a sample was removed for HPLC analysis by Method 1. The HPLC results showed a peak for hydroxystyrene (HSM) having an area of 88.7 area %, no detectable pHCA, and a total of 11.3 area % for other products as measured at a wavelength of 258 nm. At a wavelength of 312 nm some pHCA was detected. The flask containing the yellow reaction solution was removed from the oil bath. The oil bath temperature was decreased to 80° C. and the flask containing the reaction mixture was lowered back into the oil bath. Then, 0.164 g of Vazo® 67 initiator (2.8 mol %) in 0.5 mL of DMF was added to the reaction. The reaction solution was heated at 80° C. for a total of 16 h, including 4 h on one day, 7 h on the next day, and 5 h on a third day, with the heat removed between these times. During the heating period, the reaction solution changed from yellow to pale orange and became more viscous.

After the reaction solution cooled to room temperature, it was added dropwise to 60 mL of water with vigorous stirring. The precipitated material was gummy. Following 20 min of vigorous stirring, a milky liquid layer was decanted. The process of adding 60 mL of water, stirring for 20 min, and decantation was repeated twice more. Through this process, the solids became more powdery. The solids were filtered through a medium porosity funnel, washed with water, and dried on the frit of the funnel under nitrogen for 15 min. The light tan solids, with a crude weight of 3.66 g, were stored in the refrigerator.

The solids were redissolved in 20 mL of methanol, and the resulting dark yellow solution was added dropwise to 60 mL of water with vigorous stirring. Solids precipitated immediately. After 5 min of stirring, the off-white solids were filtered through a medium porosity funnel, washed with three 50 mL portions of water, and dried on the frit of the funnel under nitrogen for 2 h. The crude weight of the solids was 2.861 g.

The solids were dried in a vacuum oven overnight at a temperature of 60° C. and a pressure of 16 inches of mercury (54 kPa), yielding a final weight of off-white solid=2.664 g (72.8% yield from PHCA). $^1$H NMR was consistent with poly(4-hydroxystyrene). GPC gave Mw 10,500, Mn=3,700, Mw/Mn=2.84 (including a minor low molecular weight peak having approximately 4% of the GPC area).

Example 2

Decarboxylation of 4-Hydroxycinnamic Acid Followed by In Situ Polymerization of 4-Hydroxystyrene in N,N-dimethylacetamide The purpose of this Example was to demonstrate the synthesis of poly(4-hydroxystyrene) (PHS) in a one-pot, two-step process from 4-hydroxycinnamic acid (PHCA) in N,N-dimethylacetamide (DMAc).

4-Hydroxycinnamic acid (5.002 g) and 7 mL of N,N-dimethylacetamide (DMAc, reagent grade) were charged into a 25-mL round-bottom flask equipped with a reflux condenser, magnetic stirring, and nitrogen and the mixture was stirred at room temperature for 5-10 min until the pHCA was dissolved, producing a pale yellow solution. Then, 0.303 g of potassium acetate was added. The reaction solution was heated at 125° C. in an oil bath for 5 h. After this time a sample was removed for HPLC analysis by Method 1. The HPLC results showed a peak having a peak area of 95.22 area % hydroxystyrene (HSM), no detectable pHCA, and a total of 4.78 area % for other products as measured at a wavelength of 258 nm. The flask containing the golden yellow reaction solution was removed from the oil bath. The oil bath temperature was decreased to 80° C., and the flask containing the reaction solution was lowered back into the oil bath and the solution was stirred for 5 min. Then, 0.250 g of Vazo® 67 initiator (4.27 mol %) in 0.5 mL of DMAc was added to the reaction solution, and the solution was heated at 80° C. for 24 h. During the heating period, the reaction solution changed from golden yellow to pale orange yellow and became more viscous.

After the reaction solution cooled to room temperature, it was added dropwise to 125 mL of water with vigorous stirring over a period of 15 min. The precipitated material was gummy and semi-solid. Following 10 min of stirring, a milky liquid layer was decanted. The process of adding 100 mL of water, stirring vigorously for 15 min, and decantation was repeated twice more. Through this process, the solids became a powder. The solids were filtered through a medium porosity funnel, washed with water, and dried on the frit of the funnel under nitrogen for 10 min.

The light tan solids were redissolved in 15-20 mL of methanol, and the resulting yellow-orange solution was added dropwise to 200 mL of water with vigorous stirring over a period of 10 min. Solids precipitated immediately. After 10 min of stirring, the off-white solids were filtered through a medium porosity funnel, washed four times with 50 mL portions of water, and dried on the frit of the funnel under nitrogen overnight. The crude weight of the solids was 3.145 g.

The solids were dried in a vacuum oven overnight at a temperature of 58° C. and a pressure of 16 inches of mercury (54 kPa), yielding a final weight of a light beige solid=3.057 g. (83.5% yield from pHCA). $^1$H NMR and FTIR were consistent with poly(4-hydroxystyrene). GPC gave Mw=10,200, Mn=6,230, Mw/Mn=1.64 (not including a minor low molecular weight peak having approximately 0.5% of GPC area).

Example 3

Decarboxylation of 4-Hydroxycinnamic acid. Concentration, and In Situ Polymerization of 4-Hydroxystyrene The purpose of this Example was to demonstrate that the substrate concentration for the decarboxylation and polymerization steps may be chosen independently by adding a concentration or dilution step in a one-pot, three-step process. The first step was decarboxylation of pHCA under conditions which provided nearly quantitative yield of 4-hydroxystyrene (HSM). The second step was concentration of the resulting HSM solution by partial stripping of the DMAc solvent and the third step was polymerization of the HSM with addition of a radical initiator.

4-Hydroxycinnamic acid (9.580 g, 58.4 mmol) and 30.013 g of N,N-dimethylacetamide (DMAc, reagent grade) were charged into a 100-mL 3-neck round-bottom flask equipped with a reflux condenser, magnetic stirring, internal thermowell and thermocouple, septum inlet adapter, and nitrogen and the mixture was stirred at room temperature for 10 min. Separately, an oil bath was preheated to 153° C., and the reaction flask was lowered into the oil bath and allowed to equilibrate at 150° C. Then, 0.081 g of potassium acetate (1.4 mol %) was weighed in a drybox and added to the reaction mixture in one portion. The reaction mixture was heated for 210 min at 150° C. After this time a sample of the reaction mixture was removed for HPLC analysis by Method 2. The HPLC results indicated the presence of 0.2 mmol of pHCA and 60.4 mmol of HSM. Within experimental error, these values represent an essentially quantitative conversion of pHCA to HSM.

The flask was raised out of the oil bath, and the oil bath was allowed to cool to room temperature. The reflux condenser was replaced with a simple vacuum distillation apparatus and the flask was lowered back into the oil bath. Under reduced pressure of 300 millitorr (40 Pa), solvent was collected in a graduated collection flask. To increase the rate of solvent stripping, the oil bath temperature was increased to 40° C. and the vacuum was adjusted to 225 millitor (30 Pa). A total of 16.62 g of DMAc solvent was removed at a slow steady rate to concentrate the solution. The distillation apparatus was removed and replaced with a reflux condenser. The oil bath temperature was increased to 80° C., and the flask containing the reaction solution was lowered into the oil bath. Then, 0.450 g of Vazo® 67 initiator (4 mol %) in 1.0 mL of DMAc was added to the reaction. The reaction solution was heated at 80° C. for 24 h.

After the reaction solution cooled to room temperature, it was added dropwise to 200 mL of water with vigorous stirring for a period of 15 min. The precipitated material was gummy and semi-solid. Following 10 min of stirring, a milky liquid layer was decanted. The process of adding 150 mL of water, stirring vigorously for 15 min, and decantation was repeated twice more. Through this process, the solids became a powder. The solids were filtered through a medium porosity funnel, washed with water, and dried on the frit of the funnel under nitrogen for 10 min.

The solids were redissolved in approximately 30 mL of methanol, and the resulting solution was added dropwise to 300 mL of water with vigorous stirring over a period of 10 min. Solids precipitated immediately. After 10 min of stirring, the solids were filtered through a medium porosity funnel, washed four times with 50 mL portions of water, and dried on the frit of the funnel under nitrogen overnight. The crude weight of the solids was 5.284 g.

The solids were dried in a vacuum oven overnight at a temperature of 60° C. and a pressure of 15-20 inches of mercury (51-68 kPa), yielding a final weight of a light beige solid=5.125 g. (73.0% yield from pHCA). $^1$H NMR was consistent with poly(4-hydroxystyrene). GPC gave Mw=11,295, Mn=6,268, Mw/Mn=1.80 (not including three minor low molecular weight peaks having approximately 3% of GPC area).

Example 4

Decarboxylation of 4-Hydroxycinnamic acid. Concentration, and In Situ Polymerization of 4-Hydroxystyrene at Larger Lab Scale The purpose of this Example was to demonstrate that the substrate concentration for the decarboxylation and polymerization steps may be chosen independently by adding a concentration or dilution step in a one-pot, three-step process, as described in Example 3, but at a scale nearly twenty times as large.

4-Hydroxycinnamic acid (180.596 g, 1.100 mol) and 562.8 g of N,N-dimethylacetamide (DMAc, reagent grade) were charged into a 1-L, 4-neck round-bottom flask equipped with a reflux condenser, magnetic stirring, internal thermowell and thermocouple, septum inlet adapter, and nitrogen and the mixture was stirred at room temperature for 10 min. Separately, an oil bath was preheated to 153° C., and then raised in position to heat the reaction flask, which was allowed to equilibrate at 150° C. Then, 1.508 g of potassium acetate (1.4 mol %) was weighed in a drybox and added to the reaction mixture in one portion. The reaction mixture was heated for 210 min at 150° C. After this time, a sample of the reaction mixture was removed for HPLC analysis by Method 2. The HPLC results indicated the presence of 0.006 mol of pHCA and 1.181 mol HSM. These values are consistent with an essentially quantitative conversion of pHCA to HSM.

The oil bath was lowered from the flask, and the oil bath and flask were allowed to cool to room temperature. The reflux condenser was replaced with a short path distillation head. The oil bath was adjusted to 40° C. and was raised again to the flask. Under reduced pressure of approximately 250 millitorr (33 Pa), 282.62 g of DMAc was collected, leaving approximately 413 g of solution. A sample of the solution was analyzed using HPLC and found to have an HSM concentration of 34.46 wt %. A portion of this solution (65 g) was set aside for use in Example 5, and the remaining approximately 348 g of solution was retained in the flask for the polymerization step.

The distillation apparatus was removed and replaced with a reflux condenser. An overhead mechanical stirrer was used instead of magnetic stirring. The oil bath temperature was increased to 80° C., and the bath was raised to the flask. Then, 8.603 g Vazo® 67 initiator (4.5 mol %) in 17 mL of DMAc was added to the reaction. The reaction solution was heated at 80° C. for 24 h. Samples for GC analysis were taken after 0, 1, 2, 4, 6, 19, and 24 h, at which times the remaining HSM concentration was 100, 59.2, 35.4, 21.4, 15.1, 7.4, and 7.5% of the initial concentration, respectively, demonstrating greater than 92% conversion of the HSM to polymer. The solution also became viscous after the first few hours.

After the reaction solution cooled to room temperature, it was filtered to remove an o-ring that had deteriorated during the polymerization reaction and fallen into the solution. The solution was divided in half, and each half was precipitated into approximately 3 L of water. The precipitates were combined and washed 4 times with 3 L of water each time. After partial drying on a vacuum filter with nitrogen purge overnight, there was 209.5 g of a granular, semidry polymer. The polymer was dissolved in 630 mL of methanol. The solution was divided in half, and each half was precipitated into 4 L of water. The precipitates were combined and washed 3 times with 3 L of water each time. After drying again overnight on a vacuum filter, the dissolution in methanol and precipitation into water was repeated. Following drying over the weekend in a vacuum oven at a temperature of 65° C. and a pressure of 15-20 inches of mercury (2.0 to 2.7 kPa), the weight of off-white polymer was 107.0 g (89.2% yield from HSM solution used in the polymerization).

Example 5

In Situ Copolymerization of 4-Hydroxystyrene and Styrene

The purpose of this Example was to demonstrate that copolymers can be made by combining a comonomer with the solution of HSM produced from decarboxylation of pHCA prior to polymerization.

The HSM solution that was set aside in Example 4 (10.006 g of the 34.46 wt % HSM solution; 28.7 mmol) and 0.304 g of styrene (2.92 mmol) were charged into a 25-mL round bottom-flask equipped with a magnetic stirrer, nitrogen, and a reflux condenser. The flask containing the yellow reaction solution was lowered into an oil bath preheated at 80° C. After 10 min, 0.224 g of Vazo® 67 initiator (3.7 mol %) was added to the reaction mixture. The reaction solution became noticeably more viscous within 1 h. The reaction solution was heated at 80° C. for a total of 24 h.

After the reaction solution cooled to room temperature, it was added to 150 mL of water. The precipitated polymer was slightly tacky, but became a workable solid after 30 min of vigorous stirring. The pale yellow solid was filtered, washed three times with 100 mL portions of water, and dried on the frit of the funnel under nitrogen for 30 min. The solids were redissolved in a minimal amount of methanol (15 to 20 mL) with stirring for 10 min. The polymer solution was reprecipitated in 200 mL of water with vigorous stirring, and stirring was continued for 15 min. The off-white solids were filtered through a medium porosity funnel, washed three times with 100 mL portions of water, and dried on the frit of the funnel under nitrogen overnight. The crude weight of the solids was 3.590 g.

The solids were dried in a vacuum oven for two days at a temperature of 65° C. and a pressure of 16 inches of mercury (54 kPa), yielding a final constant weight of off-white solid 3.471 g (92.5% yield from HSM and styrene). $^1$H NMR in DMF-$d^7$ was consistent with an HSM/styrene copolymer containing 15.0 mol % of styrene. GPC gave Mw=13,200, Mn=7,090, Mw/Mn=1.86 (not including two minor low molecular weight peaks having approximately 0.7% of GPC area).

Example 6

Decarboxylation of 4-Hydroxycinnamic acid to 4-Hydroxystyrene Monomer

The purpose of this Example was to produce 4-hydroxystyrene monomer solution for subsequent concentration and polymerization.

4-Hydroxycinnamic acid (181.10 g, 1.103 mol) and 520.3 g of N,N-dimethylacetamide (DMAc, reagent grade) were charged into a 1-L, 4-neck round-bottom flask equipped with a reflux condenser, magnetic stirring, internal thermowell and thermocouple, septum inlet adapter, and nitrogen and the mixture was stirred at room temperature for 10 min. Separately, an oil bath was preheated to 153° C., and then raised in position to heat the reaction flask. During heat up, a nitrogen sweep and no condenser water were used until the internal temperature reached 120° C., after which condenser water was turned on and the nitrogen sweep was changed to a nitrogen blanket. Following equilibration of the reaction mixture at 150° C., 1.508 g of potassium acetate (1.4 mol %) was weighed in a drybox and added to the reaction mixture in one portion. The reaction mixture was heated for 180 min at 150° C. The reaction mixture was allowed to cool to room temperature, and a sample of it was removed for HPLC analysis by Method 2. The HPLC results indicated the presence of 0.010 mol of pHCA and 1.059 mol HSM. The total net weight of solution was 638.2 g. The calculated concentration of HSM in the solution is 19.94 wt %.

Example 7

Concentration of 4-Hydroxystyrene Monomer Solution

The purpose of this example was to make a concentrated 4-hydroxystyrene monomer solution and demonstrate its stability.

200.1 g of the HSM solution of Example 6 was placed into a 300 ml round-bottom flask. An oil bath was heated to 55° C. The flask was lowered into the oil bath, and a short path distillation head, vacuum, and collection flask were connected to the flask. Under reduced pressure of approximately 85 millitorr (11 Pa), 128.32 g of DMAc was collected. A sample of the remaining solution was analyzed by HPLC Method 2 and found to have an HSM concentration of 52.92 wt %. 4.15 g of fresh DMAc was added back to the solution, after which an HPLC determination by Method 2 gave an HSM concentration of 51.04 wt %. The total net weight of this solution was 76.0 g.

An aliquot of the 51.04 wt % HSM solution was stored in a refrigerator at 0° C. Its concentration was tested by HPLC several times over the next 25 days. Seven determinations averaged 51.9 wt % with a range from 49.2 to 54.2 wt %. After 169 days the concentration was 50.45%. Another aliquot was stored at 22° C., and after 28 days the concentration was 50.2%. Thus, this HSM solution has surprisingly excellent stability under these conditions.

Example 8

In Situ Polymerization of 4-Hydroxystyrene Initiated by Vazo® 52

The purpose of this Example was to demonstrate polymerization of 4-hydroxystyrene monomer using Vazo® 52 as the initiator.

The nominally 51.04 wt % HSM solution that was prepared in Example 7 (10.009 g, 42.5 mmol) was charged into a 25-mL round bottom-flask equipped with an overhead mechanical stirrer, nitrogen, and a reflux condenser. The flask was lowered into an oil bath preheated at 62° C. After 30 min, 0.633 g of Vazo® 52 initiator (6.0 mol %) was added to the reaction mixture. The reaction solution became noticeably viscous within 30 min. and very viscous after 4 h. The reaction solution was heated at 62° C. for a total of 22 h following initiator addition. Samples for GC analysis were taken after 0, ½, 1, 2, 4, 6, and 22 h, at which times the remaining HSM concentration was 100, 73.4, 55.1, 32.8, 14.3, 9.8, and 3.8% of the initial concentration, respectively, demonstrating nearly 96% conversion of the HSM to polymer. GPC of the polymer solution gave Mw=15,600, Mn=7,720, Mw/Mn=2.02.

Example 9

In Situ Polymerization of 4-Hydroxystyrene Initiated by Vazo® 88

The purpose of this Example was to demonstrate polymerization of 4-hydroxystyrene monomer using Vazo® 88 as the initiator.

The nominally 51.04 wt % HSM solution that was prepared in Example 7 (10.008 g, 42.5 mmol) was charged into a 25-mL round bottom-flask equipped with an overhead mechanical stirrer, nitrogen, and a reflux condenser. The flask was lowered into an oil bath preheated at 118° C. After 30 min, 0.626 g of Vazo® 88 initiator (6.0 mol %) was added to the reaction mixture. The reaction solution became noticeably viscous within 30 min. The reaction solution was heated at 118° C. for a total of 22 h following initiator addition. Samples for GC analysis were taken after 0, ½, 1, 2, 4, 6, and 22 h, at which times the remaining HSM concentration was 100, 23.4, 13.0, 10.9, 10.3, 9.9, and 4.1% of the initial concentration, respectively, demonstrating 96% conversion of the HSM to polymer. GPC of the polymer solution gave Mw=6,570, Mn=3,870, Mw/Mn=1.70.

Example 10

Decarboxylation of Bio-produced 4-Hydroxycinnamic Acid Followed by In Situ Polymerization of 4-Hydroxystyrene in N,N-dimethylacetamide The purpose of this Example was to demonstrate the synthesis of poly(4-hydroxystyrene) (PHS) in a one-pot, two-step process from bio-produced 4-hydroxycinnamic acid (pHCA).

The starting pHCA material was produced using a method similar to that described by Ben-Bassat et al. in U.S. patent U.S. Patent Publication No. 2005-0260724. That method involves a two-stage process to produce pHCA from glucose.

In the method used in this Example, the two stages were done as two separate steps. In the first step, tyrosine was produced from glucose by fermentation using a tyrosine overproducing strain. The tyrosine was separated from the fermentation broth using low speed centrifugation. The resulting precipitate was suspended in water and separated again using low speed centrifugation. The purity of the tyrosine was estimated to be 90-98% using HPLC. Then, in the second stage, the tyrosine was converted to pHCA at pH 10.0 using a host cell comprising an enzyme having tyrosine ammonia lyase activity. The pHCA accumulated in the reaction medium. The host cells were then separated from the reaction medium using a hollow-fiber microfiltration membrane with 0.1 micron particle diameter exclusion size. The pHCA was then recovered from the cell free reaction medium by adjusting the pH to 3.5 using 10 wt % HCl in order to precipitate the pHCA. The pHCA crystals were separated from the solution using vacuum filtration. The wet cake was washed with deionized water (mass ratio of wash water to pHCA of approximately 5:1), then dried in a vacuum oven (25 mm Hg, 80 C) for approximately 48 hours.

The bio-produced 4-hydroxycinnamic acid (10.478 g, 91.44% purity based on HPLC Method 2), and 30.014 g of N,N-dimethylacetamide (DMAc, reagent grade) were stirred vigorously for 2 h and then filtered through a medium porosity glass-fritted Buchner funnel to remove dark brown insolubles. By HPLC Method 2, a sample of the filtrate contained 23.89 wt. % pHCA.

The amber filtrate was charged to a 100 mL round-bottom flask equipped with a reflux condenser, magnetic stirring, and nitrogen. The solution was heated to 150° C. in an oil bath. Potassium acetate was added (0.084 g), and the reaction mixture was heated for 6 h. A sample was removed for HPLC analysis by Method 2 and found to contain 18.5 wt. % HSM and no pHCA.

The flask containing the amber reaction solution was placed into a preheated oil bath at 80° C. Then, 0.050 g of Vazo® 67 initiator (0.46 mole %) was added to the reaction mixture. After heating for 5.5 h, an additional 0.480 g of Vazo® 67 initiator (4.4 mole %) was added to the reaction mixture. The reaction mixture was heated for 22.5 h more (28 h total).

After the red-brown reaction solution cooled to room temperature, it was added dropwise to 300 mL of water with vigorous stirring. The precipitated material was light amber in color and gooey. Following 20 min of vigorous stirring, the milky liquid layer was decanted. The process of adding 200 mL of water, stirring for 20 min, and decantation was repeated 5 times more. Through this process, the gooey precipitate became a powdery solid.

The solids were redissolved in 30 mL of methanol, and the resulting solution was added dropwise to 300 mL of water with vigorous stirring. Light tan solids precipitated. After 5 min of stirring, the solids were filtered through a medium porosity funnel, washed with excess water, and dried on the frit of the funnel under nitrogen overnight. The solids were further dried in a vacuum oven overnight at a temperature of 70° C. and a pressure of 16 inches of mercury (54 kPa). The resulting solid chunks were pulverized with a mortar and pestle. The finely ground powder was charged to a 200 mL round-bottom flask along with 100 mL of toluene. The mixture was stirred vigorously and heated at reflux temperature for 1.5 h. The solids were filtered hot through a coarse-fritted Buchner funnel and washed with (2×100 mL) hot toluene. The solids were dried on the frit of the funnel under nitrogen overnight. The solids were further dried in a vacuum oven overnight at a temperature of 70° C. and a pressure of 16 inches of mercury (54 kPa), yielding a final weight of beige solid=4.276 g (60.4% yield from PHCA). $^1$H NMR was consistent with poly(4-hydroxystyrene). GPC gave Mw=5,860, Mn=3,500, Mw/Mn=1.67.

Example 11

Concentration of 4-Hydroxystyrene Monomer Solution and In Situ Polymerization Initiated by Peroxide The purpose of this example was to demonstrate that HSM could be polymerized using a peroxide initiator.

345 g of the HSM solution of Example 6 was placed into a 500 ml round-bottom flask. An oil bath was heated to 45° C. The flask was lowered into the oil bath, and a short path distillation head, vacuum, and collection flask were connected to the flask. Under reduced pressure of approximately 75 millitorr (10 Pa), 191 g of DMAc was collected. A sample of the remaining solution was analyzed by HPLC and found to have an HSM concentration of 45.40 wt %. 17 ml of fresh DMAc was added back to the solution, after which two HPLC determinations (40.49, 40.39) by Method 2 gave an average HSM concentration of 40.44 wt %. The total net weight of this solution was 156 g.

The nominally 40.44 wt % HSM solution (10.000 g, 33.7 mmol) was charged into a 25-mL round bottom-flask equipped with an overhead mechanical stirrer, nitrogen, and a reflux condenser. The flask was lowered into an oil bath preheated at 87° C. After 30 min, 0.289 g of Luperox® 26 initiator (4.0 mol %) was added to the reaction mixture. The reaction solution was heated at 87° C. for a total of 22 h following initiator addition. Samples for GC analysis were taken after 0, ½, 1, 2, 4, 6, and 22 h, at which times the remaining HSM concentration was 100, 92.1, 82.5, 68.5, 51.8, 44.3, and 38.6% of the initial concentration, respectively, demonstrating 61% conversion of the HSM to polymer. GPC of the polymer solution gave Mw=14,255, Mn=8,010, Mw/Mn=1.78.

Example 12

Decarboxylation of 4-Hydroxycinnamic acid Catalyzed by Sodium Carbonate, Concentration, and In Situ Polymerization of 4-Hydroxystyrene The purpose of this Example was to demonstrate that 4-hydroxystyrene (HSM) produced by sodium carbonate catalyzed decarboxylation of 4-hydroxycinnamic acid could be polymerized to polyhydroxystyrene.

4-Hydroxycinnamic acid (9.578 g, 58.3 mmol) and 30.007 g of N,N-dimethylacetamide (DMAc, reagent grade) were charged into a 100-mL 3-neck round-bottom flask equipped with a reflux condenser, magnetic stirring, internal thermowell and thermocouple, septum inlet adapter, and nitrogen and the mixture was stirred at room temperature for 10 min. Separately, an oil bath was preheated to 153° C., and the reaction flask was lowered into the oil bath and allowed to equilibrate at 150° C. Then, 0.086 g of anhydrous sodium carbonate (1.4 mol %) was weighed in a drybox and added to the reaction mixture in one portion. The reaction mixture was heated for 90 min at 150° C. After this time a sample of the reaction mixture was removed for HPLC analysis by Method 2. The HPLC results indicated the presence of 3.1 mmol of pHCA and 56.5 mmol of HSM. These values represent close to a quantitative conversion of pHCA to HSM. The HSM concentration was determined to be 18.18 wt %.

The HSM solution (36.205 g) in a 3-neck 100 ml round-bottom flask was fitted with a short path distillation head, vacuum, and collection flask. The flask was lowered into a 45°

C. oil bath, and stirring was begun. Under reduced pressure of approximately 75 millitorr (10 Pa) for several hours, 23.8 g of DMAc was collected. A sample of the remaining solution was analyzed by HPLC Method 2 and found to have an HSM concentration of 53.50 wt %. 3.985 g of fresh DMAc was added back to the solution with stirring, resulting in a final HPLC assay of 40.82 wt % HSM.

The nominally 40.82 wt % HSM solution (16.122 g, 54.8 mmol) in a 3-neck 100 mL round bottom-flask was fitted with an overhead mechanical stirrer, nitrogen, and a reflux condenser. The flask was lowered into an oil bath preheated at 85° C. After 30 min, 0.420 g of Vazo® 67 initiator (4.0 mol %) was added to the reaction mixture. The reaction solution was heated at 85° C. for a total of 22 h following initiator addition. Samples for GC analysis were taken after 0, ½, 1, 2, 4, 6, and 22 h, at which times the remaining HSM concentration was 100, 58.2, 39.8, 25.2, 18.8, 19.5, and 19.6% of the initial concentration, respectively, demonstrating 80% conversion of the HSM to polymer.

After the reaction solution (14.408 g) cooled to room temperature, it was added dropwise to 200 mL of water with vigorous stirring for a period of 30 min. The precipitated material was solid, not gummy. Following 10 min of stirring, a milky liquid layer was decanted. The process of adding 150 mL of water, stirring vigorously for 15 min, and decanting was repeated twice. Through this process, the solids became a yellowish powder. The solids were filtered through a medium porosity funnel, washed with water, and dried on the frit of the funnel under nitrogen for 10 min.

The solids were redissolved in approximately 30 mL of methanol, and the resulting solution was added dropwise to 300 mL of water with vigorous stirring over a period of 10 min. Solids precipitated immediately. After 10 min. of stirring, the solids were filtered through a medium porosity funnel, washed four times with 50 mL portions of water, and dried on the frit of the funnel under nitrogen for 30 min. The resulting wet cake had a crude weight of 15.309 g.

The solids were dried in a vacuum oven overnight at a temperature of 68° C. and a pressure of 15-20 inches of mercury (51-68 kPa), yielding a light beige solid weighing 3.736 g. (53.3% yield from pHCA, including sampling losses). $^1$H NMR was consistent with poly(4-hydroxystyrene). GPC gave Mw=10890, Mn=6055, Mw/Mn=1.80.

Example 13

In Situ Copolymerization of 4-Hydroxystyrene and t-Butyl Acrylate

The purpose of this Example was to demonstrate that copolymers can be made by combining a comonomer with the solution of HSM produced from decarboxylation of pHCA prior to polymerization.

Using the same HSM solution as described in Example 11, the nominally 40.44 wt % HSM solution (10.014 g, 33.705 mmol) and 2.304 g of t-butyl acrylate (18.257 mmol) were charged into a 25-mL round bottom-flask equipped with a magnetic spinbar, nitrogen, and a reflux condenser. Additionally, 0.265 g Vazo® 67 initiator (2.65 mole %) was added to the reaction solution. The flask was lowered into an oil bath preheated at 80° C. The reaction solution became visibly more viscous within 0.5 h. After stirring at 80° C. for 17.5 h, the heat was discontinued. The reaction solution had become very viscous and stopped stirring overnight.

After the reaction solution cooled to room temperature, an additional 10 mL of DMAc was added to the solution to decrease its viscosity, and then the polymer solution was added to 250 mL of water with vigorous stirring. Off-white solids precipitated immediately. After 20 minutes of vigorous stirring, the solids were collected by filtering through a medium-porosity, glass-fritted Buchner funnel. The solids were reconstituted to a beaker with 250 mL water and stirred vigorously for an additional 20 minutes, filtered, and washed three times with 100 mL portions of water. The solids were dried on the frit under nitrogen for 1 h and then dried further in the vacuum oven overnight at 70° C. and 16 in. mercury with a nitrogen purge, resulting in a pale yellow solid. $^1$H NMR showed the presence of residual DMAc.

The polymer was further purified by dissolving in a minimal amount of methanol and reprecipitating into 300 mL of water with vigorous stirring. The white solids were collected by filtering through a medium porosity funnel, washed three times with 100 mL portions of water, and dried on the frit of the funnel under nitrogen for 15 minutes.

The white solids were dried in a vacuum oven for two days at a temperature of 70° C. and a pressure of 16 inches of mercury (54 kPa), yielding a final constant weight of white solid=5.74 g (90.3% yield from HSM and t-butyl acrylate). $^1$H NMR in MeOD and FTIR were consistent with an HSM/t-butyl acrylate copolymer. GPC gave Mw=36,801, Mn=14,540, Mw/Mn=2.531.

Example 14

Decarboxylation of 4-Hydroxycinnamic Acid, Concentration, and In Situ Polymerization of 4-Hydroxystyrene in 1-Methyl-2-Pyrrolidinone The purpose of this Example was to demonstrate the synthesis of poly(4-hydroxystyrene) (PHS) in a one-pot, three-step process from 4-hydroxycinnamic acid (pHCA) in 1-Methyl-2-Pyrrolidinone (NMP).

4-Hydroxycinnamic acid (9.578 g) and 30.012 g of 1-methyl-2-pyrrolidinone (NMP) were charged into a 100-mL round-bottom flask equipped with a reflux condenser, magnetic stirring, and nitrogen, and the reaction mixture was stirred at room temperature for 5-10 min until the pHCA was dissolved, producing an amber solution. The flask was lowered into an oil bath preheated at 150° C. Then, 0.082 g of potassium acetate was added to the flask. The reaction solution was heated at 150° C. in an oil bath for 4 h. After this time, a sample was removed for HPLC analysis by Method 1. The chromatogram showed a hydroxystyrene (HSM) peak of 96.53 area % and no detectable pHCA as measured at a wavelength of 258 nm. The flask containing the dark amber reaction solution was removed from the oil bath.

The reaction solution was partially concentrated under reduced pressure by the same procedure as in Example 3 to produce a 35.45 wt % HSM solution as measured by HPLC Method 2.

16.010 g of the HSM solution was charged to a 50-mL round bottom flask. The flask was lowered into an oil bath preheated at 80° C. Then 0.3661 g Vazo® 67 initiator (4.03 mole %) was added to the flask and the solution was heated at 80° C. for 22 h. The polymerization resulted in a viscous, amber solution.

After the reaction solution cooled to room temperature, it was added dropwise to 250 mL of water with vigorous stirring over a period of 1 h. The resulting solids were collected by filtering through a medium-porosity, glass-fritted Buchner funnel and washed with excess water. The solids were redissolved in 30 mL MeOH and reprecipitated into 300 mL water with vigorous stirring. The solids were collected by filtering, washed with excess water, and dried on the filter under nitrogen overnight.

The solids were dried in a vacuum oven overnight at a temperature of 70° C. and a pressure of 16 inches of mercury (54 kPa), yielding a final weight of a light peach solid=4.9905 g. (87.9% yield from HSM). $^1$H NMR was consistent with poly(4-hydroxystyrene). GPC gave Mw 11,284, Mn=7,962, Mw/Mn=1.417.

Example 15

Decarboxylation of 4-Hydroxy-3-methoxycinnamic Acid Followed by In Situ Polymerization of 4-Hydroxy-3-methoxystyrene in N,N-dimethylacetamide The purpose of this Example was to demonstrate the synthesis of poly(4-hydroxy-3-methoxystyrene) in a one-pot, two-step process from 4-hydroxy-3-methoxycinnamic acid (ferulic acid) in N,N-dimethylacetamide.

Trans-4-hydroxy-3-methoxycinnamic acid (5.047 g) and 7.080 g DMAc were charged into a 50-mL round-bottom flask equipped with a reflux condenser, magnetic stirring, and nitrogen and the contents were stirred at room temperature for 15 minutes until the ferulic acid was dissolved, producing an amber solution. The flask was lowered into an oil bath preheated at 150° C. Then, 0.035 g of potassium acetate was added. The reaction solution was heated at 150° C. in an oil bath for 1 h. After this time a sample was removed for HPLC analysis by Method 1. The chromatogram showed a peak of 94.89 area % attributable to 4-hydroxy-3-methoxystyrene and no detectable ferulic acid as measured at a wavelength of 258 nm. The identification of the 4-hydroxy-3-methoxystyrene monomer was confirmed by LC/MS, (M+H)=151. The flask containing the orange-red reaction solution was removed from the oil bath.

The reaction solution was lowered into a preheated oil bath at 80° C. After 10 minutes, 0.2056 g Vazo® 67 initiator (4.38 mole %) was added to the flask and the solution was heated for 24 h at 80° C. The solution was then allowed to cool to RT.

Approximately one-half of the reaction solution (5.016 g) was worked up by adding it to 50 mL toluene with vigorous stirring. The golden-yellow supernatant was then decanted. An additional 50 mL toluene was added to the resulting gummy solid, and the mixture was again stirred vigorously and decanted. This process was repeated one more time, resulting in the formation of light tan solids. The solids were collected by filtering through a medium-porosity, glass-fritted Buchner funnel. A portion of the collected solids were saved (0.1066 g), and the remaining solids (0.7780 g) were subjected to an attempted reprecipitation from MeOH/toluene (1:10 v/v) that resulted in a gooey oil that was not isolated.

The 0.1066 g collected solids were dried in a vacuum oven overnight at a temperature of 44° C. and a pressure of 17 inches of mercury (57 kPa), yielding a final weight of the beige solid=0.0883 g. $^1$H NMR was consistent with poly(3-hydroxy-4-methoxystyrene). GPC gave Mw=13,729, Mn=8,479, Mw/Mn=1.619.

Example 16

Decarboxylation of 4-Hydroxycinnamic Acid, In Situ Polymerization of 4-Hydroxystyrene with Multiple Additions of Initiator, and Isolation and Purification of Polyhydroxystyrene by Reverse Precipitation with Water, Extraction in Hot Toluene, and Reprecipitation from Methanol Solution The purpose of this Example was to demonstrate the use of multiple additions of initiator during polymerization of 4-hydroxystyrene and the use of reverse precipitation with water and extraction in hot toluene for isolation and purification of product polymer.

4-Hydroxycinnamic acid (405.3 g, 2.436 mol) and 881.5 g of N,N-dimethylacetamide (DMAc, reagent grade) were charged into a 3-L, 4-neck round-bottom flask equipped with a reflux condenser, overhead stirring, internal thermowell and thermocouple, septum inlet adapter, and nitrogen, and the mixture was stirred at room temperature for 30 min. to dissolve the pHCA. Insolubles were removed from the solution by filtering with a coarse fritted funnel and #1 Whatman filter paper. Separately, an oil bath was preheated to 153° C., and the reaction flask was lowered into it and allowed to equilibrate at 150° C. Then, 4.788 g of potassium acetate (2.0 mol %) was weighed in a drybox and added to the reaction mixture in one portion. The reaction mixture was heated for 210 min at 150° C. After this time, a sample of the reaction mixture was removed for HPLC analysis by Method 2. The HPLC results indicated the presence of no pHCA and 2.235 mol HSM in a solution weighing 1164.7 g.

Most of the HSM solution (1137.0 g, containing 2.181 mol HSM) was charged into a 2-L, 4-neck round-bottom flask equipped with a reflux condenser, an overhead mechanical stirrer, and nitrogen blanket. The flask was lowered into an oil bath preheated to 85° C., and equilibrated for 25 min. Then, 25.340 g neat Vazo® 67 initiator (6 mol %) was added to the reaction solution. The reaction solution was heated at 85° C. for 8 h. After 2 h, an additional 6.29 g neat Vazo® 67 initiator (1.5 mol %) was added. After 4 h, an additional 3.14 g neat Vazo® 67 initiator (0.75 mol %) was added. After 6 h, an additional 1.57 g neat Vazo® 67 initiator (0.375 mol %) was added. Samples for GC analysis were taken after 0, ½, 1, 2, 4, 6, and 8 h, at which times the remaining HSM concentration was 100, 68.2, 56.7, 42.0, 23.2, 16.2, and 12.0% of the initial concentration, respectively, demonstrating 88% conversion of the HSM to polymer. The final solution had an oil-like viscosity and a weight of 1160.0 g.

After the reaction solution cooled to room temperature, it was transferred to a larger 3-neck round-bottom flask. 1 L of deionized water was added to the flask containing the solution, and the mixture was stirred vigorously for 15 min. When the stirring was stopped, solids settled to the bottom, and then a milky white supernatant was removed. The process was repeated with a second 1 L of deionized water added to the wet solids. Approximately 1.5 L of toluene was added to the flask containing the resulting wet solids, and stirring was started. The flask was lowered into an oil bath preheated at 90° C. After 1 h of heating and stirring, the polymer was allowed to settle, and the hot toluene was removed by vacuum aspiration with a glass-fritted tube. This extraction process was repeated with a second 1.5 L of toluene. After removal of liquid, most of the residual solvent was evaporated with the help of a nitrogen line. The polymer was dissolved in 1310 g of methanol. Since the solution had a slight haze, it was filtered through Whatman #2 filter paper, resulting in a clear solution. The solution was divided into 3 equal portions and each precipitated dropwise with vigorous stirring into approximately 12 L deionized water. The precipitated solids were isolated by filtration through a medium porosity glass fritted funnel, followed by slurry washing on the funnel. Solids from the 3 portions were combined, rinsed with 3 displacement washes, and dried on the filter funnel with a nitrogen blanket. The polymer was placed into glass dishes lined with PTFE film to prevent the wet polymer from sticking and dried in a vacuum oven at 6065° C. for 5 days. The final weight of off-white dried polymer was 211.7 g (80.8% yield from HSM solution used in the polymerization). $^1$H NMR was consistent with poly(4-hydroxystyrene) and showed a residual monomer content of 0.4 mole %. GPC gave Mw=4,960, Mw/Mn=1.50.

The above subject matter fully sets forth the invention and the resultant unique products therefrom. It is to be understood that the novel substituted styrenes produced in this manner can undergo further processing, including without limitation, those processes set forth in U.S. Pat. No. 6,414,110; U.S. Pat.

No. 6,593,437; U.S. Pat. No. 6,759,483; U.S. Pat. No. 6,787,611; and U.S. Pat. No. 6,864,324. All of these patents are incorporated herein by reference in toto as if they were fully set forth in this specification.

What is claimed is:

1. A process for the production of a poly(hydroxystyrene) consisting of the steps of:

a) providing a phenolic having the general structure:

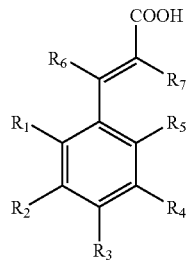

wherein $R_1$, $R_3$, and $R_5$ are H, OH, or $OCH_3$; $R_2$, and $R_4$ are H, OH, $OCH_3$ or linear or branched alkyl; $R_6$ and $R_7$ are H, halo, or cyano, provided that at least one of $R_1$, $R_3$, or $R_5$ is OH, and that $R_2$, and $R_4$ are not both simultaneously t-butyl;

b) providing a first reaction mixture comprising:
   i) a non-amine basic catalyst; and
   ii) at least one first polar organic solvent e) contacting the phenolic of (a) with the reaction mixture of (b) at a temperature and for a time sufficient for the decarboxylation of the phenolic substrate to form a stable decarboxylated hydroxystyrene intermediate, and f) contacting the decarboxylated hydroxystyrene intermediate with a second polar organic solvent and a polymerization initiator at a temperature and time sufficient to produce a poly(hydroxystyrene), with the proviso that:

the phenolic is selected from the group consisting of 4-hydroxycinnamic acid, ferulic acid, sinapinic acid, caffeic acid, 2-hydroxycinnamic acid, 3,5-dimethyl-4-hydroxycinnamic acid, and α-cyano-4-hydroxycinnamic acid, the non-amine basic catalyst is selected from the group consisting of potassium acetate, potassium carbonate, potassium hydroxide, sodium acetate, sodium carbonate, sodium hydroxide and magnesium oxide; and the first and second polar organic solvents are independently selected from the group consisting of N,N-dimethylformamide 1-methyl-2-pyrrolidinone, N,N-dimethylacetamide, dimethylsulfoxide, hexamethylphosphoramide, and hexamethylphosphorous triamide.

* * * * *